United States Patent [19]

Ailinger et al.

[11] Patent Number: 5,271,381
[45] Date of Patent: Dec. 21, 1993

[54] VERTEBRAE FOR A BENDING SECTION OF AN ENDOSCOPE

[75] Inventors: Robert E. Ailinger, Norwood; James J. Frassica, Chelmsford; Robert J. Herrington, Holland, all of Mass.

[73] Assignee: Vision Sciences, Inc., Natick, Mass.

[21] Appl. No.: 793,630

[22] Filed: Nov. 18, 1991

[51] Int. Cl.$^5$ .................................. A61B 1/00
[52] U.S. Cl. .................................. 128/4; 138/120
[58] Field of Search ............... 138/120; 128/4, 6, 7, 128/8, 772, 657, 658; 604/282

[56] References Cited

U.S. PATENT DOCUMENTS

| | | | |
|---|---|---|---|
| 2,975,785 | 3/1961 | Sheldon | 138/120 |
| 3,739,770 | 6/1973 | Mori | |
| 3,788,303 | 1/1974 | Hall | 128/4 |
| 4,726,355 | 2/1988 | Okada | |
| 4,796,607 | 1/1989 | Allred, III et al. | 138/120 X |
| 4,869,238 | 9/1989 | Opie et al. | |
| 4,947,827 | 8/1990 | Opie et al. | |
| 5,105,819 | 4/1992 | Wollschläger et al. | 128/4 X |

Primary Examiner—Richard J. Apley
Assistant Examiner—Karen A. Jalbert
Attorney, Agent, or Firm—Seed and Berry

[57] ABSTRACT

A bending section of an endoscope is constructed from non-round vertebrae. The vertebrae are D-shaped, having a planar portion and an arcuate portion. A first pair of protrusions extends from a first surface of the vertebra, defining a vertical bending axis. A second pair of protrusions extends from a second surface of the vertebra, defining a horizontal bending axis. Because the vertebra is D-shaped, the second pair of protrusions are farther from the longitudinal bending axis of the bending section than the first pair of protrusions. To provide uniform, symmetrical bending of the bending section, the first pair of protrusions are shorter than the second pair of protrusions. In addition, the first pair of protrusions extends at a different angle than the second pair and thus have a different shape, so that the first and second pair of protrusions are not symmetrically shaped with respect to each other. The asymmetrical shape of the non-round vertebra is exactly compensated for by the asymmetrical shape of the protrusions to provide symmetrical bending of the bending section. In addition, the apex of each protrusion is flat, providing a flat contact surface between adjacent vertebrae.

14 Claims, 3 Drawing Sheets

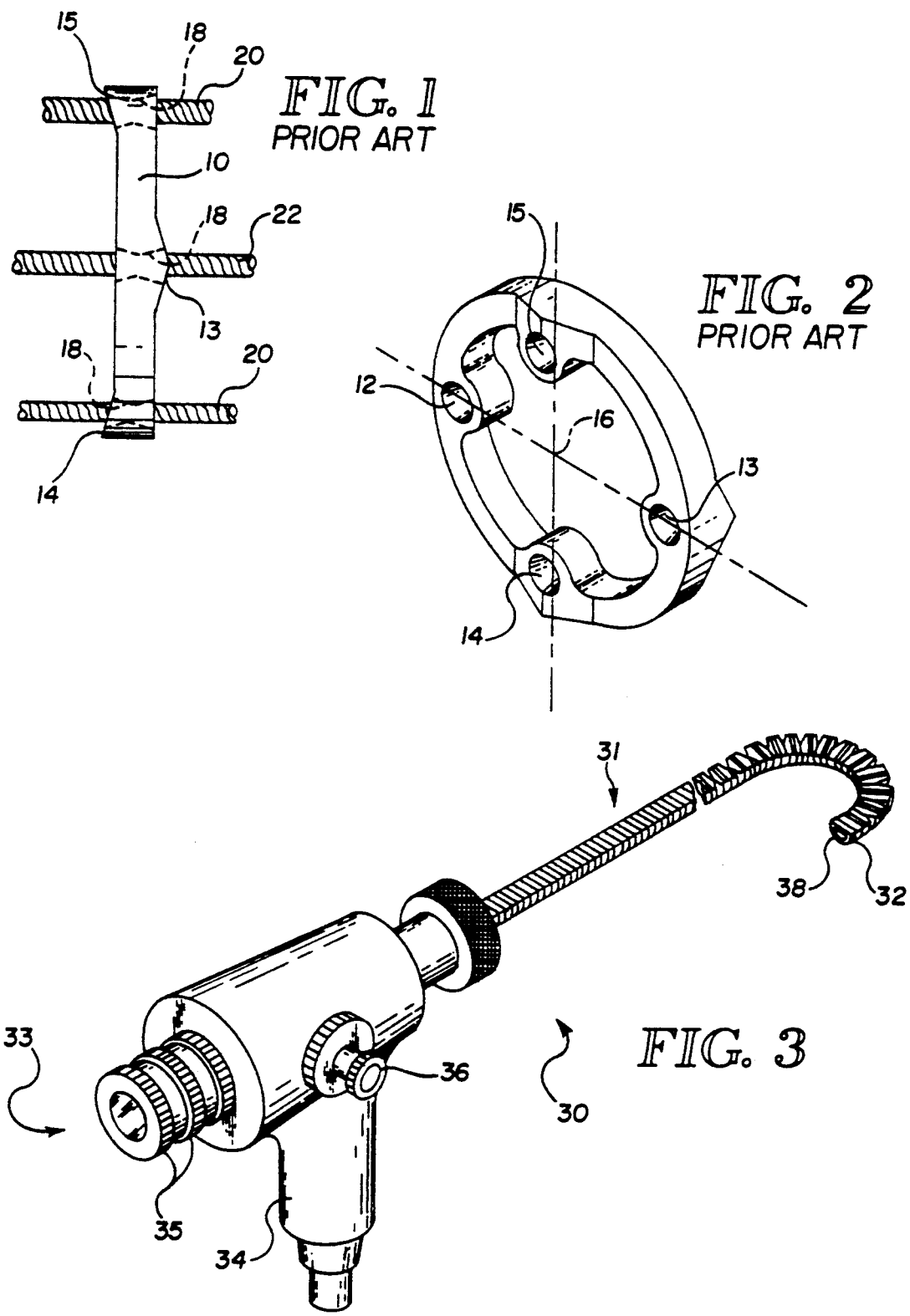

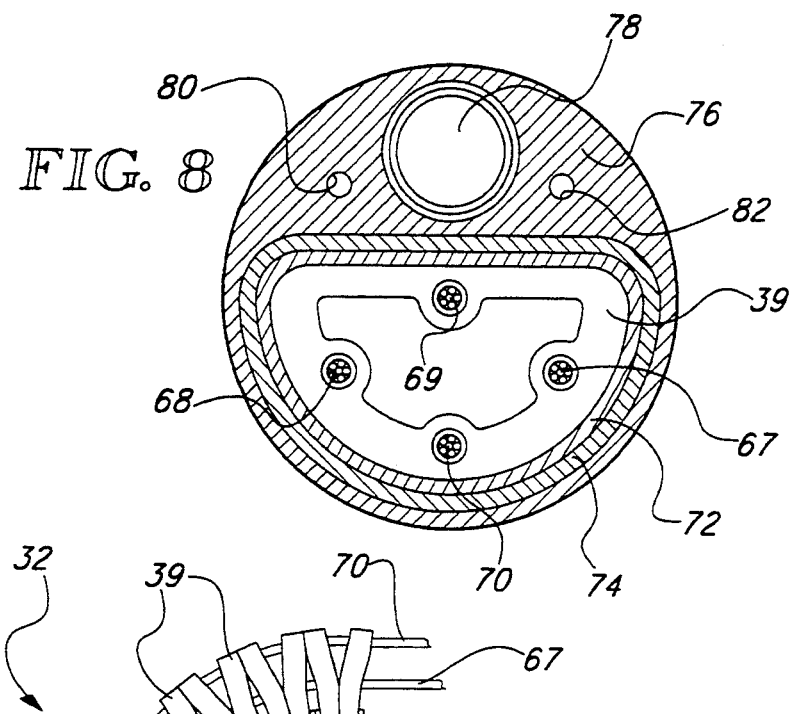
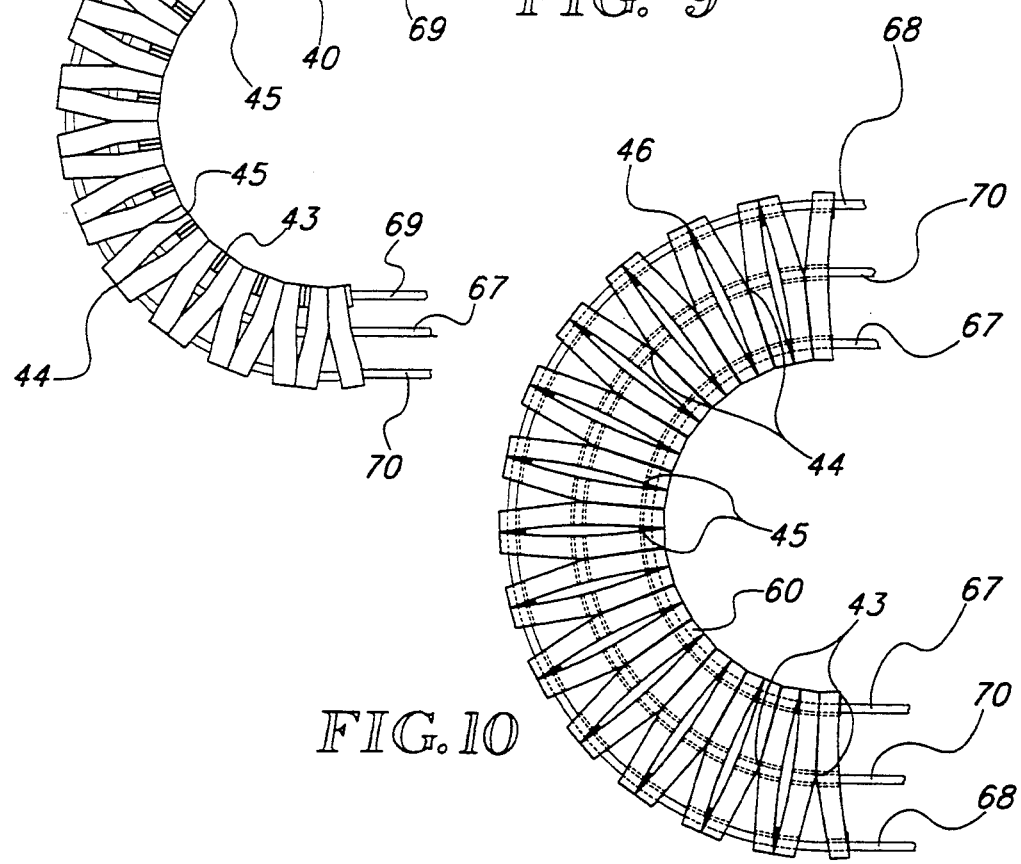

VERTEBRAE FOR A BENDING SECTION OF AN ENDOSCOPE

TECHNICAL FIELD

This invention is related to the bending section of an endoscope and, more particularly, to the shape of an individual vertebra in the bending section of an endoscope.

BACKGROUND OF THE INVENTION

An endoscope includes a handle and an insertion tube for inserting into a patient to perform diagnostic and therapeutic procedures. The insertion tube of the endoscope generally includes a bending section near the distal tip so that the orientation and position of the distal tip is steerable by a physician.

The bending section of the endoscope must be sufficiently controllable and flexible that the physician can position the tip in any necessary location within the body cavity being examined. For most endoscopes, the tip must be able to perform a 180° turn in any direction. In some types of endoscopes, the tip need turn only in a left or right direction to provide the control required by the physician.

There are many different structures which can be used in constructing the bending section of an endoscope. One structure, as described in U.S. Pat. No. 3,739,770, utilized two helically wound metal strips, one of which loosely surrounds the other. The bending section is controllably steered by at least one cable extending through the tube and connecting to a control mechanism in the housing of the endoscope.

In U.S. Pat. No. 4,947,827 (the '827 patent), the bending section is comprised of a plurality of links coupled together by pivots. The main body of the links are spaced sufficiently from each other that each link may pivot about so that the entire endoscope may bend.

U.S. Pat. No. 4,869,238 (the '238 patent), to Opie et al., describes an insertion tube comprised of three concentric helical coils of thin, spring steel ribbons. The cylindrical members are formed into a D-shaped tube 94 using a conventional press, as illustrated in FIG. 5 of the '238 patent. Ribs 170 having the desired shape including the groove 122 are then coupled to the D-shaped tube 94 to provide the final, generally circular endoscope having a groove as shown in FIG. 8 of the '238 patent. A disposable channel with a disposable sheath, as described in U.S. Pat. No. 4,646,722, is then placed within the groove to provide a circular insertion tube for insertion within the human body. A bending section similar to that shown in the '827 patent may then be used at a distal end portion to permit steering o the tip.

SUMMARY OF THE INVENTION

According to one embodiment of the invention, a bending section of an endoscope insertion tube is comprised of many individual vertebrae. The vertebrae are D-shaped in cross-section, providing a non-round bending section. A first pair of vertically spaced protrusions project from one surface of the vertebra to define a vertical bending axis for the bending section. A pair of horizontally spaced protrusions project from another surface of the vertebra to define a horizontal bending axis for the bending section. The longitudinal bending axis for the insertion tube is defined by the intersection of the horizontal and vertical bending axes.

The second pair of protrusions is spaced farther from the longitudinal bending axis than the first pair of protrusions. The protrusions are spaced different distances from the longitudinal bending axis because the vertebra is not round; it is D-shaped.

The height and shape of the protrusions are selected to provide symmetrical bending about the longitudinal axis of the bending section. The protrusions that define the horizontal axis are spaced farther from the longitudinal axis than the other protrusions that define the vertical axis. Therefore, the horizontal axis protrusions extend higher and at a steeper angle than the protrusions providing the vertical bending axis. The shape and angles of the protrusions are selected to provide symmetrical bending of the bending tip based on equal displacement by the control wires.

The apex of the protrusions is a flat surface. The vertebra contacts an adjacent vertebra on this flat surface region to provide a flat contact surface between the two vertebrae. This allows the vertebra to be positioned straight, in a stable orientation, when the tension in the cables is equal. The flat segments are less likely to wear than a curved segment and result in a more durable endoscope. In addition, there is little or no slippage at the contact surface when the bending section is articulated. In an alternative embodiment, the apex can be slightly curved, with a relatively large radius.

There are four cylindrical apertures extending through the vertebra for receiving control wires. The apertures are positioned on an inside surface, adjacent the protrusions on the first and second surfaces. Selectively retracting and extending the control wires that extend through the protrusions turns the bending section a desired degree of bend. The clearance for the control wires through the apertures is balanced with the thickness of a metal braid which covers the bending section. For smooth operation and torsional stability, the apertures are generally planar and a small clearance is provided for the control wire. Even with a small clearance, a relatively heavy braid is required to ensure that the bending section has torsional stability. Therefore, a heavy braid, generally providing 85% to 100% coverage, is used around the bending section to provide the desired torsional stability. A polymetric jacket is over the metal braid, completely enclosing the insertion tube.

BRIEF DESCRIPTION OF THE DRAWINGS

FIG. 1 is a side elevational view of a prior art vertebra of a bending section.

FIG. 2 is an isometric view of the prior art vertebra of FIG. 1.

FIG. 3 is an isometric view of an endoscope having a bending section constructed according to principles of the present invention.

FIG. 8 is a cross-sectional view of the bending section of the insertion tube of FIG. 3, with a sheath attached.

FIG. 9 is a side elevational view of the bending section curved in a 180° bend upward about a horizontal axis with a planar portion of a vertebra on the inside of the curve.

FIG. 10 is a bottom plan view of the bending section of the insertion tube in a 180° bend to the right about a horizontal axis with a curving portion of a vertebra on the inside of the curve.

DETAILED DESCRIPTION OF THE INVENTION

Figure 4:
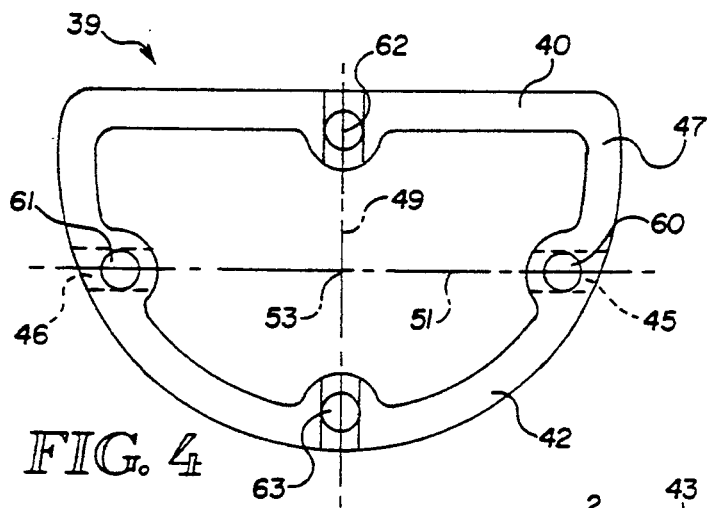
FIG. 4 is a front view of the vertebra according to one embodiment of the invention.

FIGS. 1 and 2 show a prior art vertebra 10 of a bending section of an endoscope. The prior art vertebra 10 includes a first pair of protrusions 12 and 13 extending from a first surface and defining a horizontal bending axis. Protrusions 14 and 15 extend from a second surface and define a vertical bending axis. The intersection 16 of the horizontal and vertical bending axes defines the longitudinal bending axis of the bending section of the insertion tube.

The longitudinal bending axis 16 is symmetrically located with respect to each of the protrusions 12–15. Further, each of the protrusions are symmetrical in shape. That is, protrusions 12–15 each have the same shape and dimensions.

The vertebra 10 includes four apertures 18 through which control wires 20–23 extend (FIG. 1). The slots 18 are chamfered on both sides to reduce friction between the slots and the control wires. The selective manipulation of the control wires 20 permits a bending section composed of a plurality of these vertebrae 10 to be articulated at selected angles. Each of the control wires 20–23 is retracted or extended an equal distance for the same degree of bend in all directions. For example, the control wire 22 may be retracted 1 inch to produce a selected degree of bend about the vertical axis, for example, 90°. Similarly, control wire 20 is retracted the same amount, 1 inch, to provide the same degree of bend, 90° about the horizontal axis. This provides a conventional feel for the user, such that he expects the displacement of control wires to cause the same degree of bend about either the vertical or horizontal axis.

FIG. 3 illustrates an endoscope 30 having an insertion tube 31 with a bending section 32 constructed according to principles of the present invention. The endoscope 30 includes a handle 34 having control knobs 36 which remain outside the body and are manipulated by an operator to articulate the bending section 32 of the insertion tube 31. An eye piece 33 having focusing rings 35 permits a physician to view objects at the tip of the endoscope. The insertion tube 31 is sufficiently flexible to permit it to travel through the interior of the human body within a selected body channel, such as the esophagus, the urinary tract, the large intestine, or the like.

The bending section 32 of the insertion 31 is steerable by the operator. Steering is accomplished by the operator retracting or extending control wires through manipulation of knobs 36 to move the bending section 32 up, down, left or right after the insertion tube has been advanced to the desired location in the human body. By providing bending in each of these four directions, independent of each other, the tip can be steered to any orientation about a full 360° rotation. Steering of the bending section 32 permits the operator to place the tip 38 at a selected location within the human body. The operator may then view a portion of the body through a fiber-optic cable, remove a sample for biopsy purposes, place a chemical at the selected location, or perform other medical procedures.

The bending section 32 must be sufficiently flexible to bend through at least 180° to perform selected medical procedures. To permit this controlled bending, the bending section 32 is comprised of a plurality of individual vertebrae which pivot with respect to each other.

FIGS. 4–7 illustrate the individual vertebra 39 of a bending section 32. Each individual vertebra is D-shaped. That is, the vertebra includes a generally planar portion 40 and an arcuate portion 42. A first pair of protrusions 43–44 project from a first surface 47 of the vertebra to define a vertical bending axis of said insertion tube. A second pair of protrusions 45–46 extend from a second surface 41 of the vertebra 39 to define a horizontal bending axis 51 for the insertion tube 31. The intersection of the vertical bending axis 49 and the horizontal bending axis 51 defines a longitudinal bending axis 53 for the insertion tube.

Protrusion 43 is positioned on the generally planar portion 40 and protrusion 44 is positioned adjacent the apex of the arcuate portion 42. The protrusions of the second pair 45, 46 are positioned on a curving portion of the arcuate region 42, symmetrical with respect to each other and equidistant from the protrusions 43 and 44.

As can be seen from viewing FIG. 4, the vertebra is not symmetrical about the horizontal bending axis 51. In addition, protrusions 45 and 46 are spaced a different distance from the longitudinal bending axis 53 than protrusions 43 and 44. In an alternative embodiment, the protrusions are all spaced equidistant from the bending center 53. This is possible in a D-shaped or asymmetrical vertebra by selecting the dimensions and shape of the arc portion 42 and proper positioning of all the protrusions. In the embodiment of FIG. 4, however, the protrusions are asymmetrically located with respect to the bending center 53 because they are not all spaced equidistant.

As is well known, for a given angular displacement of an object, a point far from the center of rotation moves a longer distance than a point near the center of rotation. That is, if an object rotates 90°, a point near the center of rotation may move only an inch, while a point on the object far from the center of rotation may move several inches (or several feet). The same principle applies to the asymmetrical vertebra. Apertures 62 and 63 are closer to the bending center 53 than apertures 60 and 61 are to the bending center 53. Accordingly, a given displacement of control wires 69 and 70 produces a 90° bend in the up-down direction. A greater displacement of control wires 67 and 68 would normally be required to produce the same 90° bend in left-right direction because wires 67 and 68 are farther from bending axis 53. The size and shape of protrusions 43–46 are selected to compensate for this difference, such that the same displacement of wires 67-70 produces exactly the same degree of bend in each direction. This useful feature of one embodiment is discussed in more detail with respect to FIGS. 10 and 11.

As just noted, the shape and slope of the protrusions 43–46 are selected to compensate for the asymmetrical shape of the vertebra. According to a preferred embodiment of the invention, the protrusions 45 and 46 extend slightly more from the surface 49 than protrusions 43 and 44 extend from surface 47. In addition, the angle at which protrusions 45, 46 extend is different than the angle at which protrusions 43 and 44 extend. The angles 2 and 3 are each chosen so as to achieve the same bending radius in two orthogonal planes, the horizontal and vertical planes with the disposable member in place and forming a part of the endoscope (see FIG. 8). Because of the asymmetry of the protrusion locations with respect to the longitudinal bending axis 53, the angle 2 is less than the angle 3. In one preferred embodiment, the angle 2 is 5.6° while the angle 3 is 5.8° in order to achieve symmetrical bending of the bending section. The respective angles are symmetrical about each respective protrusion. These particular angles were selected to achieve a desired bending radius and based on the actual dimensions of the vertebra shown in FIG. 4 and assuming the sheath 76 of FIG. 8 is in place. For a different vertebra of disposable member, the dimensions and angles will be different than this vertebra, and given the teachings herein a person of ordinary skill in the art would be able to construct a vertebra having the protrusions extending at the desired angle to provide symmetrical bending with an asymmetrical vertebra.

Figure 5:
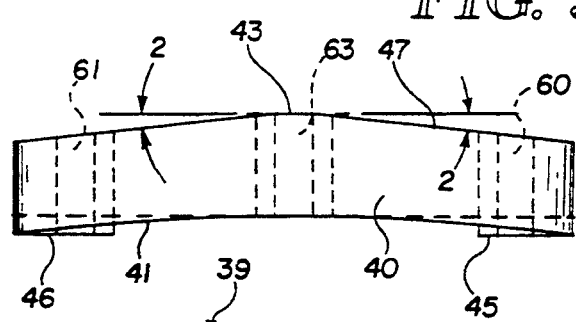
FIG. 5 is a bottom plan view of the vertebra of FIG. 4.
Figure 6:
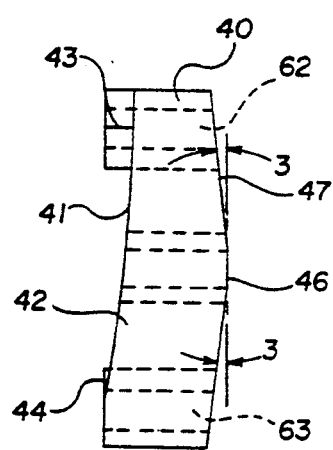
FIG. 6 is a side elevational view of the vertebra of FIG. 4.

The apex region of each of the protrusions is at a different angle than the protrusions themselves. In one preferred embodiment, the apex of each protrusion includes a flat surface region. Alternatively, the surface region is not perfectly flat, but is a curve of a large radius. The radius of the curve at the apex is different than angles 2 and 3 as shown in FIGS. 5 and 6 such that each protrusion contains at least two angles, one sloped as the protrusion extends and a different, larger curve radius at an apex surface region of each protrusion.

Adjacent vertebrae 39 contact each other at the apex of the protrusions. The flat regions on the respective protrusions of adjacent vertebrae 39 contact each other, providing a flat contact surface between the vertebrae 39. The flat surface regions allow each vertebra 39 to seat itself in a straight manner relative to the adjacent vertebra 39 by the mating contact of these flat when the tension in the control wires is equal. This allows the vertebra 39 to be positioned straight in a stable manner. The flat segments are also less likely to wear than a curved segment and results in a more durable endoscope.

Figure 7:
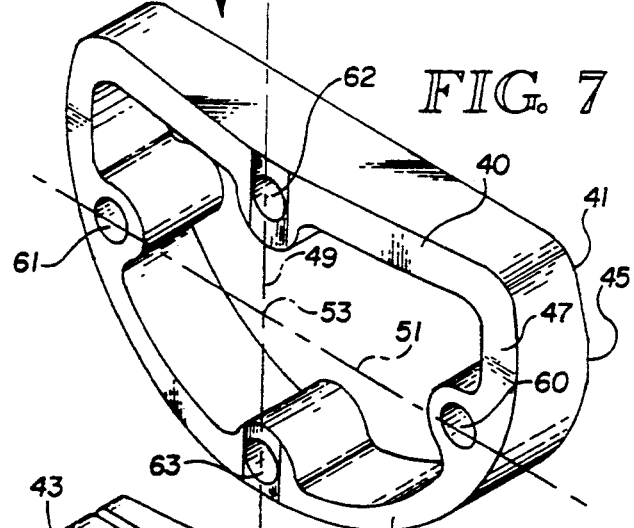
FIG. 7 is an isometric view of the vertebra of FIG. 4.

Each vertebra 39 has four apertures, 60-63. The apertures 60, 61 extend through the region adjacent protrusions 45 and 46, and apertures 62, 63 extend through the region adjacent protrusions 43 and 44. The apertures are channels through which the control wires 67-70 extend for steering the bending section of the endoscope, as shown in FIG. 7. It is not necessary that the apertures 60-63 be adjacent the protrusions. They are placed adjacent protrusions 43-46 for convenience in structure and operation and could, of course, be at a location spaced from protrusions 43-46, if desired.

In a preferred embodiment, the inside surface of apertures 60-63 is generally planar. This is compared to the prior art of FIGS. 1 and 2, in which the inside surface of apertures 18 is chamfered at both sides. Having the inside surface of the apertures generally planar, with little or no chamfer, results in better torsional stability for the bending section 32.

In one preferred embodiment, the individual vertebra 39 are about 0.1-inch thick and have relatively thin walls, for example, approximately 0.030 inch in one embodiment. The apertures 62, 63 are spaced approximately 0.10 inch from the center of bending 53 and apertures 45, 46 are spaced approximately 0.175 inch from the center of bending 53. The vertebrae are constructed by investment casting. A preferred material for the vertebrae is beryllium-copper because of its strength, fine grain structure, and tight tolerance possibilities in the investment casting procedure. An alternative material for the vertebrae is an engineering polymer, such as glass reinforced nylon impregnated with a lubricant, such as graphite.

The construction of the vertebra 39 by investment casting and from beryllium-copper is different from prior art methods for making vertebrae. For example, the vertebrae of FIGS. 1 and 2 are merely round washers which are stamped into the bowed position to allow them to rock one against the other to produce a deflection. These washers are cast flat and are later formed by coining, that is, stamping. Vertebrae constructed according to principles of the present invention in the manner described result in a high quality assembly which can be economically manufactured.

Figure 7A:
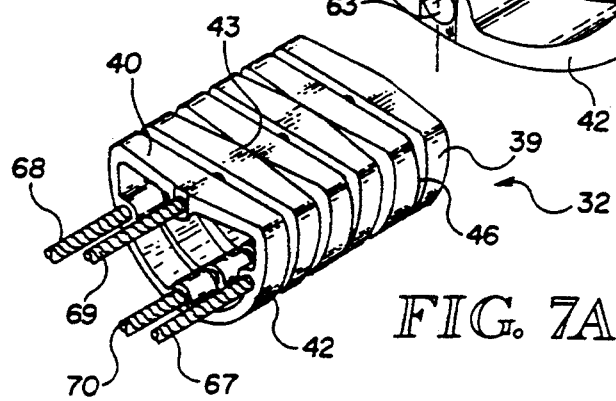
FIG. 7A is an isometric view of a bending section comprised of the vertebra of FIG. 4.

As shown in FIG. 7A, when the vertebrae are assembled into a bending section 32, the vertebrae 39 are positioned with like protrusions facing each other, in abutting contact, in the assembled bending section 32. In adjacent vertebra 39, protrusions 45 and 46 of one vertebra contact protrusions 45 and 46 of the other vertebra. Protrusions 43 and 44 extend from the other surface of the vertebra 39 and contact corresponding protrusions 43 and 44 of the vertebrae adjacent that surface. The vertebrae 39 are assembled with every other vertebra facing the same direction to provide the space for the bending section to articulate. The contact surface between two vertebrae is the flat surface region at the apex of each respective protrusion, providing the previously discussed advantages.

The bending section is articulated by retracting and extending selected control wires 67-70. Up and down bending is accomplished by retracting or extending control wires 69 and 70 as the vertebrae rock on protrusions 45 and 46. Left or right bending is accomplished by retracting or extending control wires 67 and 68, causing the vertebrae to rock on protrusions 43 and 44. By a combination of up, down, left, or right steering, tip 38 can be placed in any position around the 360° radius.

FIG. 8 is a cross-sectional view of the assembled insertion tube bending section 32 with a sheath 76 attached. The bending section 32 is composed of a plurality of individual vertebrae 39 held together by control wires 67-70 extending through respective apertures 60-63, as has previously been mentioned. The vertebrae are not mechanically coupled to each other. The tension in the control wires 67-70 extending through each vertebra 39 maintains alignment of the vertebrae.

A metal braid 72 is wrapped around the assembled vertebra 39 to form the bending section 32 of the insertion tube 31. A polymeric jacket 74 is then wrapped around the bending section 32. Typically, the polymeric jacket 74 is comprised of polyvinyl chloride or urethane. The structure of the vertebra 39 covered by the metal braid 72 and that assembly overlaid by the polymeric jacket 74 constitutes the completed bending section of the insertion tube, as shown in FIG. 3.

When the insertion tube is used to perform a medical procedure on a patient, a disposable member having a sheath 76 is positioned around the insertion tube 31, including the bending section 32. As described in U.S. Pat. No. 4,646,722, the sheath ensures that the contact surfaces with the patient are sterile for each use. The disposable member generally includes a biopsy channel 78 and air and water channels 80 and 82, respectively. The details of a sheath 76 and its attachment to and removal from an endoscope are explained in more detail in U.S. Pat. No. 4,867,238, incorporated herein by reference. Any suitable sheath 76 or method of attaching or removing such a sheath is acceptable, such a sheath generally being known in the art. Alternatively, the endoscope 31 can be used without a sheath, if desired.

The bending section is constructed to have a desired torsional stability. A high torsional stability is desired to ensure that the bending section does not rotate about the longitudinal axis 53 (as shown in FIG. 4). To provide the desired torsional stability, the clearance between control wires 67–70 and apertures 60–63 is balanced with the thickness of the metal braid 72. In one embodiment, a clearance of about 0.009 inch is provided between control wires 67–70 and apertures 60–63. Even with this relatively small clearance, there is some slop torsionally of the bending section. Preferably, a relatively heavy braid for the metal braid 72 is provided to cover the bending section 32 to increase the combined torsional stability. For example, a metal braid 72 having between 85% and 100% coverage is preferred. In one embodiment, a braid of 0.004-inch wire with eight strands of wire in the wrap is used to provide 85% to 100% coverage. In an alternative embodiment, 100% coverage is provided. (The percentage of coverage refers to the density of the wire strands, and a 100% coverage indicates that no light passes through the braid because there is a full overlap of all wire strands.)

By way of example, prior art endoscopes generally use a braid providing between 40% and 65% coverage. For example, in an Olympus endoscope, six strands are used of 0.02 diameter stainless steel and having significantly less than 85% coverage. In a Pentax endoscope, six strands having a 0.0017 diameter stainless high degree of coverage provide a coverage which is also significantly less than 85%. The high degree of coverage provided by the metal braid according to principles of the invention provides an increased torsional stability for the vertebrae of the bending section. The prior art endoscopes by Olympus and Pentax were not concerned about torsional stability because the vertebrae were coupled together at hinges rather than being held together by the control wires and the metal wrap. See, for example, U.S. Pat. No. 4,726,355 to Olympus, which shows the vertebrae being mechanically coupled together with rivets to provide hinges.

The tension in the wires 67–70 is also selected in combination with the clearance and the metal braid to provide the desired torsional stability. The tension of the wires ensures that the individual vertebrae are always retained in abutting contact with each other, and, this in combination with the use of the flat surfaces on protrusions 43–46 and the other structure of the bending section provides for high torsional stability.

FIGS. 9–10 show the bending section 32 curved through a radius of 180°, with the individual vertebra 39 shown for illustration purposes. As previously explained, control wires 67–70 extend through apertures of the individual vertebra 39. These control wires 67–70 are selectively retracted and extended to steer the bending section 32.

As illustrated in FIG. 9, the generally planar portion 40 is on an inside of the bend. To articulate the bending section 32 upward, the cable 69 is retracted and the cable 70 extended. Cables 67 and 68 are not displaced. The shape and location of protrusions 43–46 are selected to provide symmetrical bending of the bending section 32 based on symmetrical movement of each of control wires 67–70. That is, control wire 69 is retracted exactly the same distance as control wire 70. For the vertebra 39 of the present design, the length of the wire movement is essentially the same for 69 and 70 because they are located symmetrical with respect to the longitudinal bending axis 53 and protrusions 45 and 46 are identical to each other. For some non-round endoscopes, the position of the cables and the shape of protrusions 45 and 46 may be different from each other and would be selected to provide symmetrical movement of control wires 69–70.

FIG. 10 shows the bending section 32 articulated 180° turning to the right, with cable 76 on the inside of the bend. Wire 67 is retracted and wire 68 is extended to achieve the desired degree of bend. Wire 67 is retracted the same distance as wire 68 is extended as the bending section 32 is articulated. Control wire 67 is also retracted the same distance as control wire 69 for the same degree of bend.

In one embodiment, to provide a symmetrical feel to the inventive bending section 32, vertebra 39 is designed so that left and right wires are displaced the same distance as the up and down wires for the same degree of bend. As previously explained, vertebra 39 is not symmetrical in shape and protrusions 43 and 44 are physically closer to the longitudinal bending axis 53 than protrusions 45 and 46. If the protrusions were all exactly the same size and shape on this asymmetrical vertebra 39, for an equal given displacement in control wire pairs 67, 68 and 69, 70, the tip would bend a greater angle in the up/down direction then it would in the left/right direction. Therefore, protrusions 43 and 44 are made shorter than protrusions 45 and 46 to provide this symmetrical movement of the control wires. In addition, the angle at which protrusions 43 and 44 extend is less than that for protrusions 45 and 46.

The shape of angles and the size of the protrusions are selected, based on their distance from longitudinal axis 53, to provide the same degree of bend for the same displacement of the respective control wires. Thus, the distance that wire 69 is retracted for a 90° upward bend is the same distance that wire 67 is retracted for a 90° bend to the left. This results in a bending for a section that has symmetrical and uniform bending characteristics in all directions. The nonsymmetrical size and shape of the protrusions exactly compensate for the nonsymmetrical shape of the vertebra to produce symmetrical bending of the bending section 32. The bending section will thus operate in the same manner as a prior art endoscope constructed of the vertebra of FIG. 1, even though the inventive vertebra is not symmetrical. The bending section 32 thus has the same "feel" as conventional endoscopes.

Alternatively, the conventional feel may be provided with wire pairs 67, 68 and 69, 70 being displaced different lengths from each other for the same degree of bend by providing different diameter control rods as taught in U.S. Pat. No. 4,947,827, incorporated herein by reference.

An asymmetrical, non-round vertebra for use in the bending section of an endoscope has been described. The non-round vertebra is constructed to behave like a symmetrical, round vertebra. The present invention includes any vertebra constructed according to the principles of this invention and is not limited to the preferred embodiments described herein. Given the teachings herein, a person of ordinary skill in the art could construct many different vertebra designs that fall within the scope of this invention and the claims.

We claim:

1. A vertebra for use in a bending section of an insertion tube of an endoscope, comprising:
   a body member having a first surface and a second surface, the body member of the vertebra being D-shape in cross-section, said D-shape being formed by an arcuate portion extending from a substantially planar portion;
   a first pair of protrusions extending from said first surface and defining a first bending axis for said vertebra, said first pair of protrusions being aligned with said first bending axis and adapted to contact a vertebra adjacent said first surface, one of said first pair of protrusions being in said substantially planar portion and the other of said pair of protrusions being at an apex of said arcuate position;
   a second pair of protrusions extending from said second surface and defining a second bending axis for said vertebra, said second pair of protrusions being aligned with said second bending axis and adapted to contact a vertebra adjacent said second surface, said second pair of protrusions being in said arcuate portion; and
   a longitudinal bending axis for said insertion tube being defined by the intersection of said first and second bending axes, and said second pair of protrusions being spaced farther from said longitudinal bending axis than said first pair of protrusions are spaced from said longitudinal bending axis.

2. The vertebra according to claim 1, further including a plurality of cylindrical apertures extending through said vertebra on an inside surface, said cylindrical apertures being adapted to receive respective control wires for steering said bending section of said endoscope.

3. The vertebra according to claim 2 wherein said plurality of apertures includes four aperture formed in two pairs, and one of said apertures is positioned adjacent each of said protrusions on an inside surface of said vertebra, one pair of said apertures being a different distance from said longitudinal bending section than the other pair of apertures.

4. The vertebra according to claim 2 wherein said apertures are cylindrical along an inside surface and substantially parallel to said longitudinal bending axis along their entire length to increase the torsional stiffness of said insertion tube.

5. A vertebra for use in a bending section of an insertion tube of an endoscope comprising:
   a body member having a non-round cross-sectional shape;
   a pair of apertures extending through said body member, said pair of apertures being adapted to receive control cables for steering said bending section;
   a pair of protrusions extending from a first surface region of said body member, said first pair of protrusions having an angled region and an apex region, said protrusions being adapted to contact an adjacent vertebra on said apex region, said apex region having a curvature that is less than said angled region;
   a second pair of protrusions extending from a second surface of said body member, said pair of protrusions having an angled region that is at a different angle than said first pair of protrusions; and
   a pair of control wires extending through said apertures for causing said vertebra to pivot with respect to said adjacent vertebra by selectively retracting at least one of said control wires.

6. The vertebra according to claim 5 wherein said apex region has a curvature of zero, such that it is flat and said protrusions of adjacent vertebra contact each other along mutually flat surfaces.

7. The vertebra according to claim 5 wherein said apex region has a curvature of a large radius and said angled region is angled at less than 7° with respect to the target to the apex.

8. The vertebra according to claim 5 wherein said vertebrae are constructed by investment casting.

9. A bending section of an endoscope constructed from a plurality of vertebrae joined together comprising:
   a vertebra having a body member and including a first surface and a second surface generally parallel to said first surface, said body member being asymmetrical about at least one plane normal to said surfaces;
   a first pair of protrusions having a selected size and extending from said first surface a selected distance, said first pair of protrusions being aligned with a first bending axis to define said first bending axis for said vertebra, and adapted to contact a vertebra adjacent said first surface;
   a second pair of protrusions having a selected size and extending from said second surface a selected distance, said second pair of protrusions being aligned with a second bending axis to define said second bending axis for said vertebra, and adapted to contact a vertebra adjacent said second surface, the size and shape of said second pair of protrusions being different than the size and shape of said first pair of protrusions and extending for a shorter selected distance;
   a plurality of cylindrical apertures extending through said vertebra on an inside surface of said body member, said cylindrical slots being adapted to receive respective control wires for steering said bending section of said endoscope;
   a plurality of control wires extending through said apertures for selectively steering said bending section; and
   a longitudinal bending axis for said bending section being defined by the intersection of said first and second bending axes, and said second pair of protrusions being spaced farther from said longitudinal bending axis than said first pair of protrusions are spaced from said longitudinal bending axis based on said body member being asymmetrical, and the size of said second pair of protrusions being selected to provide uniform bending of said insertion tube for equal displacement of said first and second pairs of control wires.

10. The vertebra according to claim 9 wherein each of said protrusions include a flat surface region at an apex of said protrusions, said flat surface region being positioned for contacting an adjacent vertebra such that contact of the two vertebra occurs on a flat surface when said bending section is straight.

11. The vertebra according to claim 9 wherein said plurality of apertures includes four apertures formed in two pairs, and one of said apertures is positioned adjacent each of said protrusions on an inside surface of said vertebra, one pair of said apertures being a different distance from said longitudinal bending section than the other pair of apertures.

12. The bending section according to claim 9 wherein said first pair of protrusions is a different shape than said second pair of protrusions, each of said pair of protrusions extending at different respective angles from said respective surface regions.

13. The bending section according to claim 9, further including a metal braid wrapped around said bending section said metal braid providing greater than 85% coverage of said vertebra and wrapped at a selected tension to ensure proper torsional stiffness of bending section.

14. A bending section of an endoscope constructed from a plurality of vertebra joined together, comprising:
   a plurality of a vertebra, each of said vertebra having
      a body member having a first surface and a second surface;
      a first pair of protrusions extending from said first surface and defining a first bending axis for said vertebra, said first pair of protrusions being aligned with said first bending axis and contacting an adjacent vertebra on said first surface; and
      a second pair of protrusions extending from said second surface and defining a second bending axis for said vertebra, said second pair of protrusions being aligned with said second bending axis and contacting an adjacent vertebra on said second surface;
   four cylindrical apertures positioned as two pairs extending through each of said vertebra on an inside surface, said cylindrical apertures having respective control wires extending therethrough to join said vertebra together and for steering said bending section of said endoscope, each of said apertures being positioned adjacent respective protrusions on the inside surface of said vertebra, one pair of said apertures being a different distance from a longitudinal bending section than the other pair of apertures;
   a sloped surface extending away from said first pair of protrusions on said first surface at a first selected angle; and
   a sloped surface extending away from said second pair of protrusions of said second surface at a second selected angle, said second selected angle being less than first selected angle and said angles being selected such that said each pair of control wires move the same distance as each other to produce a selected degree of bend even though said respective pairs of wires are spaced different distances from said longitudinal bending axis, the longitudinal bending axis for said insertion tube being defined by the intersection of said first and second bending axes, and the second pair of protrusions being spaced farther from the longitudinal bending axis than said first pair of protrusions are spaced from the longitudinal bending axis.

* * * * *

UNITED STATES PATENT AND TRADEMARK OFFICE
CERTIFICATE OF CORRECTION

PATENT NO. : 5,271,381
DATED : December 21, 1993
INVENTOR(S) : Robert E. Ailinger et al.

It is certified that error appears in the above-indentified patent and that said Letters Patent is hereby corrected as shown below:

In claim 3, column 9, line 36, after "includes four" and before "formed", please delete "aperture" and substitute therefor --apertures--.

In claim 5, column 9, line 62, after "member, said" and before "pair of", please insert --second--.

Signed and Sealed this

Thirty-first Day of May, 1994

Attest:

BRUCE LEHMAN

*Attesting Officer*  *Commissioner of Patents and Trademarks*